United States Patent [19]
Baker

[11] Patent Number: 5,242,378
[45] Date of Patent: Sep. 7, 1993

[54] ADJUSTABLE LEG BRACE

[76] Inventor: Robert W. Baker, 15644 Wagon Wheel N., Granger, Ind. 46530

[21] Appl. No.: 878,907

[22] Filed: May 6, 1992

[51] Int. Cl.$^5$ .............................................. A61F 3/00
[52] U.S. Cl. ........................................ 602/23; 602/26; 602/27
[58] Field of Search ................ 602/26, 23, 27, 16; 128/DIG. 15, 80 C, 80 F

[56] References Cited

U.S. PATENT DOCUMENTS

| | | | |
|---|---|---|---|
| 612,087 | 10/1898 | Boyd | 602/23 |
| 1,418,283 | 6/1922 | Cameron | 602/23 X |
| 2,558,986 | 7/1951 | Seelert | 602/16 |
| 2,573,866 | 11/1951 | Murphy | 602/23 X |
| 3,230,952 | 1/1966 | Terron | 602/23 X |
| 4,494,534 | 1/1985 | Hutson | 602/16 |

Primary Examiner—Richard J. Apley
Assistant Examiner—Beverly A. Meindl

[57] ABSTRACT

An orthopedic brace for supporting the leg of a person. The orthopedic brace has a calf member connected to a thigh member by a knee joint and to a foot member by an ankle joint. Linkage located between the calf member and ankle joint is automatically adjustable during installation on the leg of a person to match the distance between the knee joint and ankle joint with the distance between the knee and ankle of the person.

15 Claims, 2 Drawing Sheets

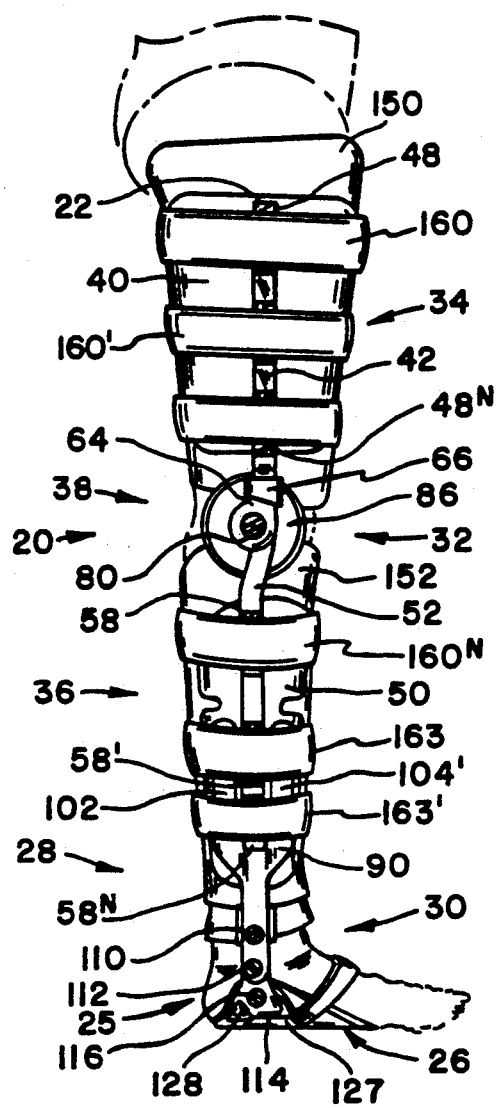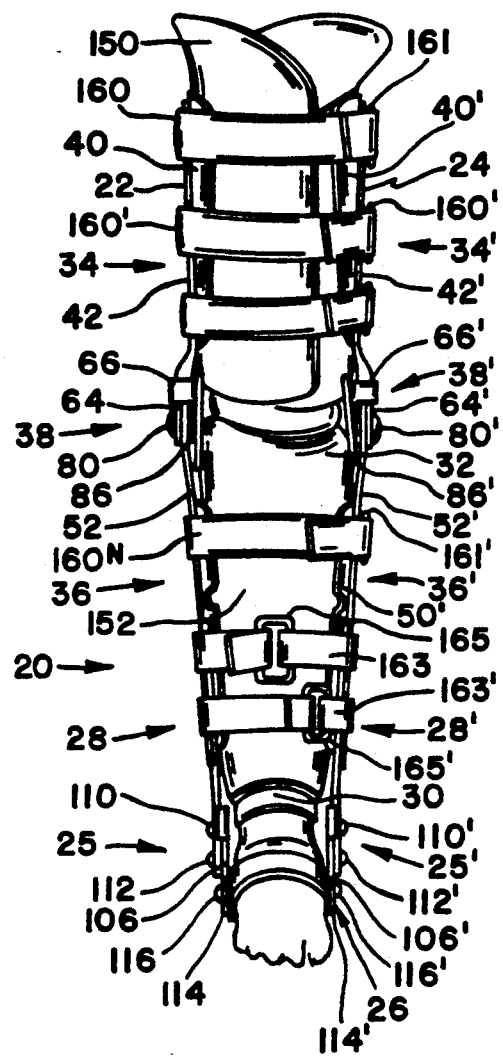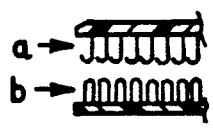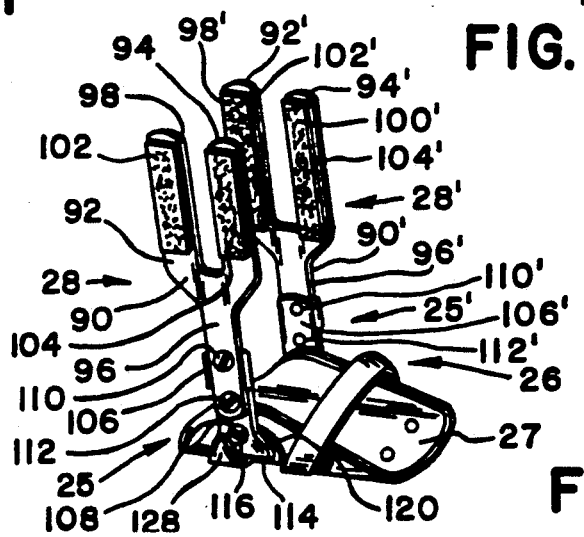
FIG. 1
FIG. 2
FIG. 12
FIG. 3

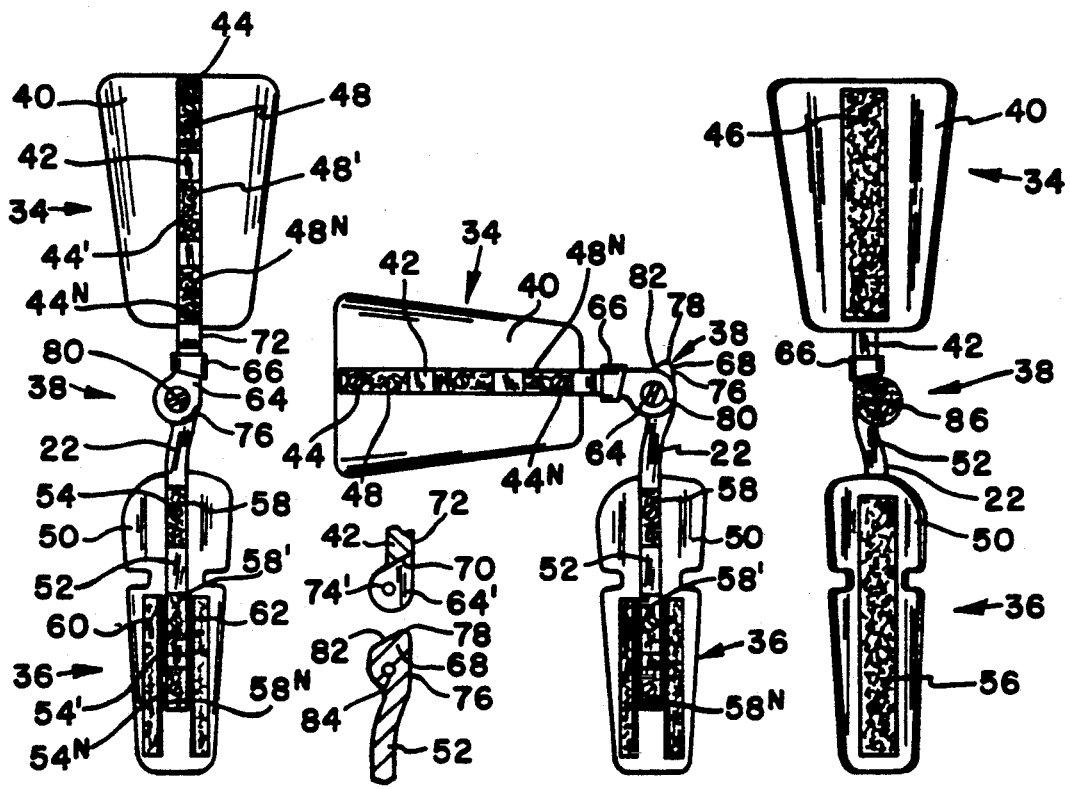
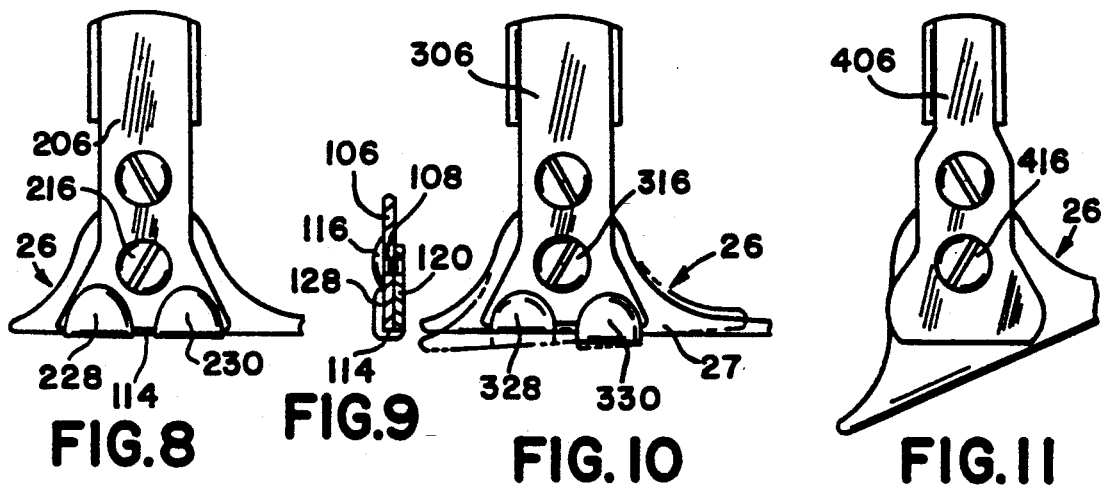

ADJUSTABLE LEG BRACE

This invention relates to a leg brace having linkage located between a calf member and an ankle joint which is automatically adjustable to substantially match the distance between the ankle joint and a knee joint with the knee and ankle of a person.

It is well known that healing of damaged limbs and joints of a person can be accelerated if the joint or limbs are immobilized or supported during a healing period. Orthesis devices can provide such support and are well known as evidenced by many prior art devices such as the following U.S. Pat. Nos. 3,785,372; 3,844,279; 4,111,194 and 4,494,534 which illustrate structure for supporting the leg of a person. Orthesis devices can be made of a variety of structural components depending on the extent and severity of an injury to the person. An example of a most extreme orthesis device for supporting a leg would be a full leg cast made from a rigid material that would completely immobilize the leg while an elastic material wrap may be considered to be a minimum supporting device. In between these extremes, various structural devices disclosed in the above identified patents offer a physician a variety of braces which can be adapted to meet the individual needs of a person. Unfortunate each orthesis device must be customized to match the person, since the length of the legs of each individual are different. U.S. Pat. No. 4,494,534 discloses a typical orthesis device wherein calf staves are joined to thigh and ankle staves through a knee and ankle joint to form a substantially fixed linear brace member for a person. While this type orthesis devices does provide ease in the installation on a leg, a physician must spend considerable time and effort to make sure that brace accurately fits the leg of an individual.

The present invention discloses an orthopedic device which is substantially customized for an individual merely by being attached to the the leg of a person. The orthopedic device which has a calf member connected to a thigh member by a knee joint and to a foot member by an ankle joint includes linkage located between the calf member and ankle joint. The linkage is automatically adjustable during installation on the leg of a person to match the distance between the knee joint and ankle joint with the distance between the knee and ankle of a person. The linkage includes a yoke member which is attached to the ankle joint. The yoke member has a first plurality of strips thereon which are made from a material having hooks extending therefrom. The calf member has a shield with second plurality of strips thereon made of a material having loops extending therefrom. When the first and second strips are joined together, a rigid connection occurs between the yoke and shield to define a fixed linear structure between the ankle and knee joint which corresponds to the distance between the knee and ankle of the person.

It is an object of this invention to provide an orthopedic device which is lightweight weight, simple to attach to the leg of a person and easily adapts to the length of the leg of an individual.

It is another object of this invention to provide an orthopedic device which is substantially customized to the leg of a person merely by attaching the device to the leg.

It is another object of this invention to provide a universal leg brace system for controlling the motion of a knee joint while allowing a desired flexibility of an ankle joint.

It is a further object of this invention to provide a lightweight orthopedic device which can be used to immobilize the leg of a person while allowing selective flexibility to allow a person to assume a sitting position with the leg in less than a linear position.

These object and many more should be apparent from reading the following specification while viewing the drawings wherein:

FIG. 1 is a side view of an orthopedic brace made according to the principles of the present invention;

FIG. 2 is a front view of the orthopedic brace of FIG. 1;

FIG. 3 is a perspective view of linkage attached to the ankle joint of the orthopedic brace of FIG. 1 which permits matching the length between the ankle joint and knee joint with the distance between the knee and ankle of a person;

FIG. 4 is an outside view of a thigh member and calf member of the orthopedic brace of FIG. 1 in a linear position;

FIG. 5 is a partial sectional view of a knee joint which is located between the thigh member and calf member of FIG. 4;

FIG. 6 is a view of the thigh member of FIG. 4 in a pivoted position with respect to the knee joint;

FIG. 7 is an inside view of the thigh member and calf member of the orthopedic joint of FIG. 1;

FIG. 8 is side view of another ankle joint for the orthopedic brace of FIG. 1 which inhibits movement between the foot member and ankle joint;

FIG. 9 is a sectional view through a pivot pin of the ankle joint of FIG. 3;

FIG. 10 is side view of another ankle joint for the orthopedic brace of FIG. 1 which allows limited movement between the foot member and ankle joint;

FIG. 11 is a side view of still a further ankle joint which allows unlimited movement between the foot member and ankle joint; and FIG. 12 is a sectional view of first and second straps one of which has hooks extending therefrom and the other has loops extending therefrom, the first and second straps are joined together to form a fixed member.

One of the first acts which occurs when a person injures a limb such as a leg is to support or immediately immobilize the limb. Most people have witnessed sport events where a player has been injured and attendants rush to investigate the injury and provide assistance. Often when a leg injury occurs some type of structure is immediately attached to the leg to prevent movement. A most common type structure is simply parallel flat boards that are secured to the leg by straps or more recently an inflatable sleeve which surrounds the leg. After a physician has had the opportunity to examine the leg, a more permanent orthesis device may be recommended to aid in the healing of the injury. Heretofor it was necessary for the physician to send the person to laboratory to have an orthesis device individualize since the length of the legs of each person are different. However, with the orthesis device 20 of the present invention disclosed and illustrated in FIGS. 1 and 2, a physician can automatically match the orthesis device 20 with the leg of a person.

The orthesis device 20 shown in FIGS. 1 and 2 is made up of an outer 22 and inner 24 brace members which are connected to a foot member 26 by linkage 28, 28'. Linkage 28, 28' allows the length of the outer 22 and inner 24 brace members to automatically matched with the distance between the length of a knee 32 and ankle 30 of the person.

The structural components of the outer 22 and inner 24 brace members are identical and therefor only the details for thigh member 34, calf member 36 and knee joint 38 for the outer brace member 22 as illustrated in FIGS. 4, 5, 6 and 7 is hereinafter described. However, where appropriate similar components in the inner brace member 24 will be identified by the same member with ' added. Further, in those instances in this specification where a series, such as X, X'... $X^n$, is recited for a plurality of similar components the value of $X^n$ is at least three.

Thigh member 34 has a shield 40 which is attach to a longitudinal bar 42 by a plurality of screws 44, 44'... $44^n$ as shown in FIG. 4. A longitudinal strip 46 of material having hooks, as illustrated by "a" in FIG. 12, is attached to the inner side of shield 40 as shown in FIG. 7 while a series of strips 48, 48'... $48^n$ of material having loops, as illustrated by "b" in FIG. 12, are attached to the longitudinal bar 42 as shown in FIGS. 4 and 6.

Calf member 36 has a shield 50 which is attached to a longitudinal bar 52 by a series of screws 54, 54'... $54^n$. A longitudinal strip 56 of the hooks material "a" illustrated in FIG. 12 is attached to the inner side of shield 50 as shown in FIG. 7 while a series of strips 58, 58'... $58^n$ of the loops material "b" are attached to the longitudinal bar 52 as shown in FIGS. 4 and 6. Further, strips 60 and 62 of the hooks material "a", which are parallel to longitudinal bar 52, are also attached to the outer surface of shield 50 as shown in FIG. 4.

The knee joint 38 is made up of a clevis 64 which is attached to longitudinal bar 42 and a tongue 68 which extends from longitudinal bar 52, a pivot pin 80 and a ring lock 66. Clevis 64 has an inner face 70 that extends at an angle less that 90° from face 72 of the longitudinal bar 42 as shown in FIG. 5. The openings 74, 74' of the clevis 64 are offset from an axial center of the longitudinal bar 42 to allow flexing or bending of the knee without placing a lateral force thereon. The tongue 68 has a face 82 that extends from apex 78 on face 76 of longitudinal bar 52. The angle of face 82 from apex 78 is complementary to face 70 of clevis 64 such that when pivot pin 80 is placed in openings 74 in the clevis 64 and opening 84 in tongue 68 and longitudinal bars 42 and 52 are parallel, face 70 engages face 82 to form a substantially straight line corresponding to the leg of a person.

The ring lock 66 which is located on longitudinal bar 42 surrounds the clevis 64 and engages tongue 68 to hold longitudinal bars 42 and 52 in substantial straight line with the leg of the person. Ring lock 66 can be moved on longitudinal bar 42 to allow longitudinal bar 42 to pivot on pin 80 with respect to longitudinal bar 52 and allow the leg of the person to bend at the knee joint without the introduction of a strain on the knee joint of the person.

A pad 86 as shown in FIG. 6 is attached to pin 80 to cushion the knee joint 38 when the outer brace member is place on a person.

Linkage 28, 28' is made of yokes 90, 90' which are attached to ankle joints 25, 25' is best illustrated in FIG. 3. Yokes 90, 90' have first 92, 92' and second 94, 94' legs, respectively, that extend from stems 96, 96' fixed to ankle joints 25, 25'. A plurality of strips 98, 100, 98', and 100', all made from the same hooks material "a" illustrated in FIG. 12, are located on inside of the first 92, 94 and second 92', 94' legs while a plurality of strips 102, 104, 102' and 104', all made from the same hooks material "b" illustrated in FIG. 12, are located on the outside of the first 92, 94 and second 92', 94' legs.

Ankle joints 25, 25' include rectangular members 106, 106' which are fixed to stems 96, 96' by screws 110, 112 and 110', 112' respectively. Rectangular members 106, 106' have opening 108, 108' therein which are located adjacent a flared base 114, 114'. The foot member 26 has a plate 27 which is adapted to engage the bottom of the foot of the person. Plate 27 has projections 120, 120' which extend therefrom with tangs 128, 128' that engage the bottom of the flared base 114, 114' as illustrated in FIG. 9. Pivot pins 116, 116' extends through openings 108, 108' to join plate 27 to the rectangular members 106, 106'. Tangs 128, 128' engage the flared bases 114, 114' to prevent foot member 26 from rotating beyond an angle that is substantially perpendicular to the stem 96, 96' to prevent dragging the foot when walking with the orthesis device 20 placed on the leg of a person.

Should a person suffer some paralysis which effects the ankle joint, it is important that the foot be retained in a plane that is substantially perpendicular to the leg. A therapist can select a variety of rectangular members such as rectangular member 206 shown in FIG. 8 in which the foot is held stationary, rectangular member 306 shown in FIG. 10 in which the foot is allowed to have limited movement and rectangular member 406 shown in FIG. 11 in which the foot is allowed unlimited movement. All these rectangular members are interchangeable by on ankle joints 25,25' through the removal of pivot pins 116, 166' from plate 27. Where appropriate, the various structural components in rectangular members 206, 306 and 406 are identified by the same numbers of rectangular member 106, 106' with a corresponding change in the prefix member.

In rectangular member 206 shown in FIG. 8, their are two tangs or flanges 228, 230 that extend from plate 27 and engage the bottom of flared end 114 to prevent any rotation of the foot member 26 with respect to pivot pin 216. In this situation, the ankle of a person would be immobilized.

In rectangular member 306 shown in FIG. 10, while their, are two tangs or flanges 328, 330 that extend from base or plate 27 of foot or sole member 26, tang or flange 330 is offset to allow limited movement as indicated by the dash lines. With rectangular members 306, 306' attached to the ankle joints 25, 25' the foot member 26 of the orthesis device 20 can rotate about pivot pins 316, 316', as illustrated by the dashed line, until tang or flange 330 engages flared bases 114, 114'.

In rectangular member 406, pivot pin 416 which is attached to projection 120 of plate allows unlimited rotation of foot member 26 with respect to the ankle joint 25.

METHOD OF ASSEMBLY

When a physician, therapist or other health care giver desires to place the orthesis device 20 on a person, a thigh pad 150 made of a foam material is wrapped around the thigh and a calf pad 152 made of a foam material is wrapped around the calf of a person, see FIGS. 1 and 2. Thereafter, the knee joints 80, 80' on the outer 24 and inner 22 brace members are aligned with the knee of the person. The hooks on strips 46, 46' and 56, 56' engage the pads 150 and 152 to hold the knee joint 80, 80' in position while a plurality of straps 160, 160'... $160^n$ are wrapped around shields 40, 40' and 50, 50'. Straps 160, 160'... 160$^n$ are made of layers of nylon material, the inner layer has strips of the hooks material "a" as in FIG. 12 located thereon. The strips on the straps 160, 160'... 160$^n$ engage strips 48, 48'... 48$^n$ on longitudinal bars 42, 42' and 52, 52' and after the ends pass through corresponding buckles 161, 161'... 161$^n$, the ends are fixed through the engagement of the hooks and loops with each other. Thereafter, foot member 26 is placed against the foot of the person and strips 98, 100, 98' and 100' on the inside of yokes 90, 90' brought into engagement with strips 60, 62 and 60', 62' on shields 50, 50' with the longitudinal bars 52, 52' being located between legs 92, 94 and 92', 94'. The hooks on strips 98, 100, 98' and 100' engage the loops on strips 60, 60', 62, and 62' to fix the foot member 26 to the outer 22 and inner 24 brace members. Thereafter straps 163, 163' which also have strips of the hooks material "a" as illustrated in FIG. 12 are wrapped around shields 50, 50' and yokes 90, 90'. The ends of straps 163, 163' are passed through buckles 165, 165' and hooks thereon engage loops to secured the straps 163, 163' and assure that the ankle joints 25, 25' remain at a fixed distance with respect to the knee joints 38, 38'.

After the orthesis device 20 is attached to the person, a leg will be supported such the sufficient weight is taken off the knee and ankle joints of the person to allow for the person to walk. When the person desires to sit down, the lock rings 66, 66' are moved with respect to the clevises 64, 64' and to allow longitudinal bars 42, 42' to pivot about pins 80, 80' and allow bending of the knee.

Thus, the orthesis device 20 disclosed herein offers support for the leg of a person while providing structure that matches the physical requirement of any person without customization of the components.

I claim:

1. An orthopedic brace for providing support to the leg of a person, said brace having a thigh member, a calf member and a foot member, said calf member being connected to said thigh member by a knee joint and to said foot member by an ankle joint, the improvement comprising:

a first shield fixed to said calf member, said first shield having a plurality of strips attached thereto, said first plurality of strips being made of a material having either hooks or loops extending therefrom;

linkage means including a yoke having a second plurality of strips attached thereof, said second plurality of strips being made of a material having either hooks or loops extending therefrom, said first and second plurality of strips being attached to each other through the engagement of said hooks and loops to connect said yoke to said shield and correspondingly said ankle joint with said calf member, said engagement of said first and second plurality of strips being adjustable during installation on the leg of the person to automatically match the distance between said knee joint and said ankle joint with the distance between the knee and ankle of the person; and first strap means which engages said yoke to aid in maintaining said engagement of said first and second plurality of strips to prevent movement of said yoke with respect to said calf member and to hold said calf member against the leg of the person.

2. The orthopedic brace as recited in claim 1 wherein said yoke includes:

first and second legs that extend from a stem fixed to said ankle joint, said first and second legs being aligned with a first longitudinal bar of said calf member, said second plurality of strips being located on said first and second legs such that a first portion engages said shield and a second portion engages said first strap means.

3. The orthopedic brace as recited in claim 2 wherein said knee joint includes:

a clevis extending from a second longitudinal bar of said thigh member, said clevis having a first face therein which extends at an angle with respect to said longitudinal bar;

a tongue extending from said first longitudinal bar of said calf member, said tongue having a second face thereon that extends from an apex;

first pin means extending through said clevis and said tongue, said first pin means allowing said second longitudinal bar to pivot with respect to said first longitudinal bar, said second face on said tongue means engaging said first face on said clevis to limit the movement of said second longitudinal bar to a position where said first and second longitudinal bars are in substantial axial alignment; and ring means located on said second longitudinal bar, said ring means engaging said clevis and tongue to hold said first and second longitudinal bars in substantial axial alignment with the leg of the person, said ring means being moved on said second longitudinal bar to allow said second longitudinal bar to pivot on said first pin means with respect to said first longitudinal bar and allow the leg of the person to bend at the knee joint.

4. The orthopedic brace as recited in claim 3 wherein said ankle joint includes:

a rectangular member attached to said stem of said yoke, said rectangular member having an opening therein adjacent a flared end thereon;

a sole member having a base that engages the bottom of the foot of the person and a projection that extends from said base at a substantially perpendicular angle; and second pin means extending through said opening in said rectangular member and secured to said projection to join said sole member to said rectangular member.

5. The orthopedic brace as recited in claim 4 wherein said sole member freely rotates on said second pin means with respect to said rectangular member.

6. The orthopedic brace as recited in claim 5 wherein said sole member further includes:

a first flange extending from said base that engages said flared end to limit said rotation said base with respect to said rectangular member.

7. The orthopedic brace as recited in claim 6 wherein said sole member further includes:

a second flange extending from said base that engages said flared end, said first and second flanges preventing rotation of said base with respect to said rectangular member.

8. The orthopedic brace as recited in claim 7 wherein said strap means includes:

second strap means which engages said second rectangular bar and a second shield to hold said thigh member against the thigh of the person.

9. An orthesis device having brace members connected to a foot member through an ankle joint for providing support to the leg of a person, the improvement in said brace members comprising:

a shield fixed to said calf member, said shield having a first plurality of strips attached thereto, said first plurality of strips being made of a material having either hooks or loops extending therefrom; and yoke means attached to said ankle joint having a second plurality of strips attached thereto, said second plurality of strips being made of a material having either hooks or loops extending therefrom, said first and second plurality of strips being attached to each other through the engagement of said hooks and loops to connect said yoke means to said shield and correspondingly said ankle joint with said calf member, said engagement of said first and second plurality of strips being adjustable during installation on the foot member on the foot of the person to align the ankle joint with the ankle of the person.

10. The orthopedic brace as recited in claim 9 further including:

strap means which engages said yoke means to aid in maintaining said engagement of said first and second plurality of strips to prevent movement of said yoke means with respect to said shield and to hold said calf member against the leg of the person.

11. The orthopedic brace as recited in claim 10 wherein said yoke means includes:

first and second legs that extend from a stem fixed to said ankle joint, said first and second legs being aligned with a first longitudinal bar of said calf member, said second plurality of strips being located on said first and second legs such that a first portion engages said shield and a second portion engages said strap means.

12. The orthopedic brace as recited in claim 11 wherein said ankle joint includes;

a rectangular member attached to said stem of said yoke means, said rectangular member having an opening therein adjacent a flared end thereon;

a foot member having a base that engages the sole of the foot of the person and a projection that extends from the base at a substantially perpendicular angle; and pin means extending through said opening in said rectangular member and secured to said projection to join said foot member with said rectangular member.

13. The orthopedic brace as recited in claim 12 wherein said foot member freely rotates on said pin means with respect to said rectangular member.

14. The orthopedic brace as recited in claim 13 wherein said foot member further includes:

a first flange extending from said base that engages said flared end to limit said rotation of said base with respect to said rectangular member.

15. The orthopedic brace as recited in claim 14 wherein said foot member further includes:

a second flange extending from said base that engages said flared end, said first and second flanges preventing rotation of said base with respect to said rectangular member.

* * * * *